US008680046B2

(12) United States Patent
Sandrock et al.

(10) Patent No.: US 8,680,046 B2
(45) Date of Patent: Mar. 25, 2014

(54) INHIBITORS OF VIRAL INTEGRASE AND METHODS OF USE

(75) Inventors: Tanya Sandrock, Salt Lake City, UT (US); Robert Craigie, Silver Spring, MD (US)

(73) Assignees: Integratech Proteomics, LLC, Salt Lake City, UT (US); The United States of America, as represented by the Secretary of the Department of Health and Human Services, Washington, DC (US)

( * ) Notice: Subject to any disclaimer, the term of this patent is extended or adjusted under 35 U.S.C. 154(b) by 0 days.

(21) Appl. No.: 13/257,550

(22) PCT Filed: Mar. 18, 2010

(86) PCT No.: PCT/US2010/027870
§ 371 (c)(1),
(2), (4) Date: Nov. 1, 2011

(87) PCT Pub. No.: WO2010/108040
PCT Pub. Date: Sep. 23, 2010

(65) Prior Publication Data
US 2012/0094896 A1    Apr. 19, 2012

Related U.S. Application Data

(60) Provisional application No. 61/161,469, filed on Mar. 19, 2009.

(51) Int. Cl.
| *A01N 37/18* | (2006.01) |
| *A61K 38/00* | (2006.01) |
| *A61P 31/18* | (2006.01) |
| *A61P 31/12* | (2006.01) |
| *A61K 38/10* | (2006.01) |
| *A61K 38/16* | (2006.01) |
| *C12Q 1/70* | (2006.01) |
| *C12Q 1/68* | (2006.01) |
| *A61K 38/04* | (2006.01) |
| *C07K 5/00* | (2006.01) |
| *C07K 7/00* | (2006.01) |
| *C07K 16/00* | (2006.01) |
| *C07K 17/00* | (2006.01) |
| *C07K 1/00* | (2006.01) |
| *C40B 30/04* | (2006.01) |
| *A61K 38/03* | (2006.01) |
| *C07K 7/02* | (2006.01) |
| *C07K 7/08* | (2006.01) |
| *A61K 39/00* | (2006.01) |
| *C07K 4/00* | (2006.01) |
| *G01N 33/573* | (2006.01) |

(52) U.S. Cl.
CPC .................. *A61K 38/00* (2013.01); *A61K 38/03* (2013.01); *C07K 7/02* (2013.01); *C07K 7/08* (2013.01); *A61K 39/00* (2013.01); *C07K 4/00* (2013.01); *G01N 33/573* (2013.01); *A61K 38/10* (2013.01); *C12Q 1/70* (2013.01); *C40B 30/04* (2013.01); *C12Q 1/68* (2013.01); *C07K 1/00* (2013.01)
USPC ............. 514/3.8; 514/1.1; 514/3.7; 514/21.4; 514/21.5; 435/5; 435/6.13; 530/326; 530/345; 506/9

(58) Field of Classification Search
None
See application file for complete search history.

(56) References Cited

U.S. PATENT DOCUMENTS

2006/0123505 A1    6/2006    Kikuchi
2008/0206742 A1    8/2008    Kalpana

FOREIGN PATENT DOCUMENTS

CN          1010207A10 A        8/2007
WO       WO2008/068765 A2    6/2008

OTHER PUBLICATIONS

Armon-Omer A, et al., "Correlation between shiftide activity and HIV-1 integrase inhibition by a peptide selected from a combinatorial library," J Mol Biol. 376(4):971-82 (2008).
UniProt Accession Q9TM11, May 1, 2000; retrieved on Jul. 5, 2012, retrieved from the internet: http://www.uniprot.org/uniprot/Q9TM11.
Extended European Search Report in corresponding European application No. EP2408803 mailed Jun. 12, 2012, 9 pages.
Office Action for Application No. CN 201080012573.6 dated Aug. 12, 2013.
Cotelle, "Patented HIV-1 integrase inhibitors (1998-2005)", Recent Patents on Anti-Infective Drug Discovery, 1:1-15 (2006).
John, et al., "Development and Application of a High-Throughput Screening Assay, for HIV-1 Integrase Enzyme Activities",. J. of Biomolecular Screening, 10 (6):606-14 (2005).
Li and Craigie, "Processing of viral DNA ends channels the HIV-1 integration reaction to concerted integration", J Biol. Chem., 280(32):29334-9 (2005).
Li, et al., "Retroviral Retroviral DNA integration: reaction pathway and critical intermediates", EMBO J., 25(6):1295-304 (2006).
EMBL Accession No. CM000440, "*Fusobacterium nucleatum* subsp. *polymorphum* ATCC 10953 chromosome, whole genome shotgun sequence," submitted Jul. 1, 2006, retrieved on Nov. 14, 2013. Retrieved from the internet: http://www.ebi.ac.uk/ena/data/view/CM000440.
Genbank Accession CP001071, "*Akkermansia muciniphila* ATCC BAA-835, complete genome," submitted May 1, 2008, retrieved on Nov. 14, 2013. Retrieved from the Internet: http://www.ncbi.nlm.nih.gov/nuccore/CP001071.

*Primary Examiner* — Marcela M Cordero Garcia
*Assistant Examiner* — Thea D'Ambrosio
(74) *Attorney, Agent, or Firm* — Meunier Carlin & Curfman, LLC

(57) ABSTRACT

Described herein are compositions and methods for inhibiting HIV integrase activity. Also described are methods of identifying agents that inhibit HIV integrase for use in treating or preventing HIV. Also disclosed are methods of identifying agents that inhibit HIV viral mutants that are resistant to integrase inhibitors.

15 Claims, 6 Drawing Sheets

INHIBITORS OF VIRAL INTEGRASE AND METHODS OF USE

CROSS REFERENCE TO RELATED APPLICATIONS

This application is a national phase filing under 35 U.S.C. §371 of PCT/US2010/027870 filed under the Patent Cooperation Treaty on Mar. 18, 2010, which claims priority to and benefit of U.S. Provisional Patent Application No. 61/161,469, filed on Mar. 19, 2009, by Tanya Sandrock and Robert Craigie, the contents of each being hereby incorporated by reference in their entirety.

REFERENCE TO SEQUENCE LISTING

The Sequence Listing submitted Sep. 19, 2011 as a text file named "INTP_01_PCT_ST25.txt," created on Aug. 12, 2011, and having a size of 1,461 bytes is hereby incorporated by reference.

BACKGROUND

According to published statistics, over 40 million people are estimated to be infected with Human Immunodeficiency Virus (HIV)/Acquired Immunodeficiency Syndrome (AIDS) worldwide and approximately 22 million people have died from AIDS (CDC, 2000 international Statistics). To combat this epidemic, exhaustive research has focused on either inhibiting the molecular mechanisms of this virus or treating the symptoms associated with it.

While AZT was the pioneer drug first prescribed for this malady, numerous drugs such as protease inhibitors, additional nucleoside analogue transcriptase inhibitors, or non-nucleoside reverse transcriptase inhibitors have become available in recent years. Because of their improved effectiveness, these drugs mark great strides in treating HIV and AIDS. Even though these drugs have shown promise in controlling viral infection, reservoirs of infected cells remain and possibly give rise to resistant variants. For example, many of these drugs do not cross the blood/brain barrier efficiently, which allows for unchecked replication and transmission throughout the following cells in the brain: capillary endothelial cells, astrocytes, macrophages (microglia), oligodendrocytes, choroid plexus, ganglion cells, neuroblastoma cells, glioma cells, and neurons. The consequences of CNS infection include neurologic and psychiatric complications such as dementia, cognitive disorders, major depression, psychosis, and polyneuropathies.

In addition to the drugs mentioned above, much research has focused on the inhibition of HIV integrase (IN), an enzyme that facilitates HIV DNA integration into the genome. However, because in vitro reactions occur in an aggregated rather than a soluble system, IN has proven rather problematic to study. It is theorized that within a cell IN performs (1) a 3'-end processing step of HIV DNA in which two nucleotides are cleaved from the 3' end of the viral DNA and (2) strand transfer reaction in which the 3' ends of the viral DNA are ligated to the target DNA. To function properly, it is believed that IN must assemble into a complex with viral DNA, host DNA, and additional viral and host protein factors. To date, numerous strand transfer inhibitors of IN have been found which include raltegravir (also known as Isentress or MK 0518), diketo analogues such as S-1360, L-870, 810, and GS-9137, and naphthyridione GSK 36473 (Philippe Cotelle, Recent patents on Anti-Infective Drug Discovery, 1:1-15 (2006)). However, due to IN mutations, HIV may become resistant to these drugs thus resulting in high failure rates and inefficient treatment.

While drugs for treating HIV and AIDS have been identified, there is a need for novel drugs that inhibit HIV integrase and for drug-screening methods that rapidly allow for the screening of peptides or small molecules that interact with and either inhibit or reduce IN activity.

BRIEF SUMMARY

In accordance with the purpose of this invention, as embodied and broadly described herein, this invention relates to compositions and methods for inhibiting HIV integrase activity. Also described are methods of identifying agents that inhibit HIV integrase for use in treating or preventing HIV. Additional advantages of the disclosed composition(s) and method(s) will be set forth in part in the description that follows, and in part will be understood from the description, or may be learned by practice of the disclosed composition(s) and method(s). The advantages of the disclosed composition(s) and method(s) will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed methods and compositions and together with the description, serve to explain the principles of the disclosed methods and compositions.

DETAILED DESCRIPTION

Figure 1:
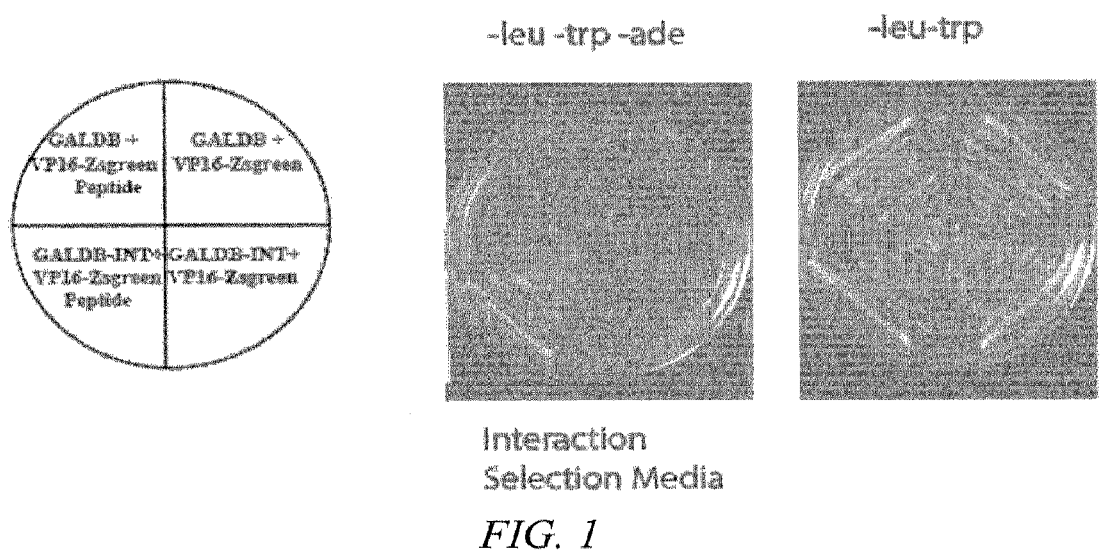
FIG. 1 shows a yeast two-hybrid screen in which growth on -ade plates indicate activation of a selectable reporter.

The disclosed methods and compositions may be understood more readily by reference to the following detailed description of particular embodiments and the Example included therein and to the Figures and their previous and following description.

Before the present compounds, compositions, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

Disclosed are materials, compositions, and components that can be used for, can be used in conjunction with, can be used in preparation for, or are products of the disclosed composition(s) and method(s). These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a peptide is disclosed and discussed and a number of modifications that can be made to a number of molecules including the peptide are discussed, each and every combination and permutation of peptide and the modifications that are possible are specifically contemplated unless specifically indicated to the contrary. Thus, if a class of molecules A, B, and C is disclosed as well as a class of molecules D, E, and F and an example of a combination molecule, A-D is disclosed, then even if each is not individually recited, each is individually and collectively contemplated. Thus, in this example, each of the combinations A-E, A-F, B-D, B-E, B-F, C-D, C-E, and C-F is specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed, it is understood that each of these additional steps can be performed with any specific embodiment or combination of embodiments of the disclosed methods, and that each such combination is specifically contemplated and should be considered disclosed.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within the ranges as if each numerical value and sub-range is explicitly recited. As an illustration, a numerical range of "about 1 to 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc. as well as 1, 2, 3, 4, and 5, individually. The same principle applies to ranges reciting only one numerical value as a minimum or a maximum. Furthermore, such an interpretation should apply regardless of the breadth of the range or the characteristics being described.

Those skilled in the art will recognize, or be able to ascertain using no more than routine experimentation, many equivalents to the specific embodiments of the composition(s) and method(s) described herein. Such equivalents are intended to be encompassed by the appended claims.

It is understood that the disclosed composition(s) and method(s) are not limited to the particular methodology, protocols, and reagents described as these may vary. It is also to be understood that the terminology used herein is for the purpose of describing particular embodiments only and is not intended to limit the scope of the present invention which will be limited only by the appended claims.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Unless defined otherwise, all technical and scientific terms used herein have the same meanings as commonly understood by one of skill in the art to which the disclosed methods and compositions belong. Although any methods and materials similar or equivalent to those described herein can be used in the practice or testing of the present method and compositions, the particularly useful methods, devices, and materials are as described. Publications cited herein and the materials for which they are cited are hereby specifically incorporated by reference. No admission is made that any reference constitutes prior art. The discussion of references states what their authors assert, and applicants reserve the right to challenge the accuracy and pertinency of the cited documents.

It must be noted that as used herein and in the appended claims, the singular forms "a," "an," and "the" include plural referents unless the context clearly dictates otherwise. Thus, for example, reference to "a peptide" includes a plurality of such peptides, reference to "the peptide" is a reference to one or more peptides and equivalents thereof known to those skilled in the art, and so forth.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed, then "less than or equal to 10" as well as "greater than or equal to 10" is also disclosed. It is also understood that the throughout the application, data are provided in a number of different formats, and that these data represent endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units is also disclosed. For example, if 10 and 15 are disclosed, then 11, 12, 13, and 14 including non-integer values in between are also disclosed.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

In this specification and in the claims that follow, reference will be made to a number of terms that shall be defined to have the following meanings:

"Optional" or "optionally" means that the subsequently described event or circumstance can or cannot occur, and that the description includes instances where the event or circumstance occurs and instances where it does not. For example, the phrase "optionally a therapeutic agent" means that the therapeutic agent can or can not be included.

Throughout the description and claims of this specification, the word "comprise" and variations of the word, such as "comprising" and "comprises," means "including but not limited to" and is not intended to exclude, for example, other additives, components, integers or steps.

As used herein, "subject" refers to a mammal, including humans, who are at risk for or have been infected with a virus including a retrovirus such as HIV and benefits from the methods and compositions described herein.

As used herein, "viral integrase" refers to an enzyme produced by a virus, including a retrovirus such as HIV, that enables or facilitates viral DNA integration into target DNA including genomic DNA of an infected cell or tissue.

As used herein, "protein domain" refers to a portion of a protein, portions of a protein, or an entire protein showing structural integrity; this determination may be based on amino acid composition of a portion of a protein, portions of a protein, or the entire protein. For example, HIV integrase may be divided into three domains which include an N-terminus portion, a central core, and a C-terminus portion.

As used herein, the term "peptide" may be used to refer to a natural or synthetic molecule comprising two or more amino acids linked by the carboxyl group of one amino acid to the alpha amino group of another. The peptide is not limited by length; thus "peptide" can include polypeptides and proteins.

As used herein, the term "nucleic acid" may be used to refer to a natural or synthetic molecule comprising a single nucleotide or two or more nucleotides linked by a phosphate group at the 3' position of one nucleotide to the 5' end of another nucleotide. The nucleic acid is not limited by length, and thus the nucleic acid can include deoxyribonucleic acid (DNA) or ribonucleic acid (RNA).

As used herein, the term "variant" refers to an amino acid or peptide sequence having conservative amino acid substitutions, non-conservative amino acid substitutions (i.e. a degenerate variant), substitutions within the wobble position of each codon (i.e. DNA and RNA) encoding an amino acid, amino acids added to the C-terminus of a peptide, or a peptide having 60%, 70%, 80%, 90%, or 95% homology to SEQ ID NO:1, SEQ ID NO:2, SEQ ID NO:3, or SEQ ID NO:4 as described herein.

As used herein, the term "small molecule" refers to small organic compounds, inorganic compounds, or any combination thereof that inhibits or reduces viral integrase activity; this term may include monomers or primary metabolites, secondary metabolites, a biological amine, a steroid, or synthetic or natural, non-peptide biological molecule(s).

As used herein, "reduce" refers to lowering enzymatic activity associated with, for example, viral integrase by 5%, 10%, 20%, 30%, 40%, 50%, 60%, 70%, 80%, 90%, or 99% including non-integer values in between when compared to a positive control As used herein, "inhibit" refers to lowering enzymatic activity associated with, for example viral integrase by 80%, 85%, 90%, 95%, 99%, or 100% including non-integer values in between when compared to a positive control.

The term "prevent" as used herein does not require absolute forestalling of the condition or disease but can also include a reduction in the onset or severity of the disease or condition. Thus, if a therapy can treat a disease in a subject having symptoms of the disease, it can also prevent that disease in a subject who has yet to suffer some or all of the symptoms.

As used herein, "measuring" refers to a process of determining the quantity or abundance of enzymatic activity (i.e. viral integrase or strand transfer complex (STC) activity) in regard to integrating viral DNA into target DNA, whether relative or absolute.

As used herein, "displace" refers to interrupting a molecular or chemical interaction between, for example, a protein domain and a peptide, a protein domain and a chemical, a protein domain and a nucleic acid sequence by a chemical, peptide, or nucleic having affinity for that specific protein domain than the peptide, chemical, or nucleic acid being displaced.

A. Compositions

1. Peptides

Disclosed herein are purified peptides that bind and inhibit HIV integrase (IN). In some aspects, the peptide comprises the amino acid sequence SEQ ID NO:1 (LeuTyrGluThrIleLeuIleLeuLeuPheLeuAspValAspThrGly), SEQ ID NO:2 (LeuTyrGluThrIleLeuIleLeuLeuPheLeuAspValAspThrGlyLysLysArg), or SEQ ID NO:3 (LeuTyrGluThrIleLeuIleLeuLeuPheLeuAspValAspThrGlyAspGluAsp). In some aspects, the peptide comprises the amino acid sequence SEQ ID NO:4 (LeuTyrGluThrIleLeuIleLeuLeuPheLeuAspValAspThrGly XaaXaaXaa), where Xaa is any amino acid. In some aspects, Xaa is a hydrophobic, hydrophilic amino acids.

In some aspects, the peptide comprises an amino acid sequence that is at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% homologic to SEQ ID NO:1, SEQ ID NO:2, or SEQ ID NO:3. Thus, in some aspects, the peptide comprises a conservative variant of amino acid sequence SEQ ID NO:1, SEQ ID NO:2, or SEQ ID NO:3. For example, the conservative variant can comprise a conservative amino acid substitutions at one or more of the amino acid residues in SEQ ID NO:1, SEQ ID NO:2, or SEQ ID NO:3. Thus, the conservative variant can comprise a conservative amino acid substitutions at 1, 2, 3, 4, 5, 6, 7, 8, 9, 10, 11, 12, 13, 14, 15, or 16 of the amino acid residues in SEQ ID NO:1, SEQ ID NO:2, or SEQ ID NO:3.

As used herein in reference to a specified amino acid sequence, a "conservative variant" is a sequence in which a first amino acid is replaced by another amino acid or amino acid analog having at least one biochemical property similar to that of the first amino acid. In addition, conservative variant and variant may be used synonymously throughout this application. To further clarify, similar properties include, for example, similar size, charge, hydrophilicity, hydrophobicity, or hydrogen-bonding capacity.

Peptide sequences can be modified for many reasons, such as enhanced solubility, potency, and longer chemical half-life. For example, SEQ ID NO:2 and SEQ ID NO:3 have basic and acidic tails at their respective C-termini respectively, which encompass the final three amino acids (LysLysArg and AspGluAsp respectively) of each amino acid sequence. These tails function to enhance solubility. In this aspect, as reflected by SEQ ID NO:4, multiple combinations of amino acids can be used to enhance stability or solubility. For example, hydrophobic, hydrophilic, basic, acidic, polar, non-polar, aromatic, and aliphatic amino acids can be readily combined and optimized to enhance peptide stability. In addition, the tail length may be readily varied in length to further optimize peptide stability. For example, the amino acid tail length may range from 1-20 amino acids, 2-15 amino acids, 3-10 amino acids, or 3-6 amino acids. Also, these combinations can include a series of polar amino acids, a series of non-polar amino acids, a series of basic amino acids, a series of acidic amino acids, a series of aromatic amino acids, a series of aliphatic amino acids In one aspect, the peptide may be modified for use in various assays. For example, peptides may be modified by radio-labeling; addition of a fluorophore; addition of specific epitopes or tags such as a glutathione S-transferase (GST) tag, a myc tag, a FLAG tag, or a 6-His tag; coupling to a solid support such as beads, the wells of a microtiter plate, or a slide; coupling to an enzyme which allows colorimetric detection, such as horseradish peroxidase or alkaline phosphatase, or tagged with a chemi-luminescent tag and used in various assays including Enzyme-linked Immunoabsorbent assays (ELISA), fluorescence polarization (FP) assays, Förster resonance energy transfer (FRET), bioluminescence resonance energy transfer (BRET), surface-enhanced Ramen spectroscopy (SERS), electrochemiluminescent immunoassays, and PCR-enhanced immunoassays to further identify or probe for specific molecular interactions (Terpe K, Applied Microbiol Biotechnol 60:523-533 (2003)); (Amal Elfaitouri et al, Clinical and Diagnostic Laboratory Immunology 12:235-241 (2005)); U.S. Pat. No. 5,266,498—Ligand binding assay for an analyte using surface-enhanced scattering (SERS) signal; U.S. Pat. No. 5,376,556—Surface-enhanced Raman spectroscopy immunoassay which is incorporated by reference herein. Such molecular interactions include, but are not limited to, protein-protein interactions, protein-peptide interactions, protein-peptide-small molecule interactions, or protein-peptide-nucleic acid sequence interactions. Also, the methods mentioned above may be useful in screening chemical libraries for chemicals or small molecules that interact with or bind at least one domain of viral integrase. In another aspect, these methods may be adapted for high-throughput screening.

Also disclosed are nucleotide sequences (i.e. genomic DNA, cDNA, unmodified mRNA, and post-transcriptionally modified mRNA) that encode the amino acid sequences disclosed herein. This would include all conserved and degenerate sequences related to a specific amino acid sequence, i.e. all nucleotide sequences having a sequence that encodes one particular peptide as well as all nucleotides, including degenerate nucleotides, encoding the disclosed variants and derivatives of the amino acid sequences.

Also disclosed is a nucleic acid vector comprising a nucleic acid encoding one or more of the peptides disclosed herein operatively linked to an expression control sequence. Also disclosed are cells comprising these vectors that are capable of producing the protein encoded by the nucleic acid when cultured.

2. Internalization Sequences

The disclosed peptide can further constitute a fusion protein or otherwise have additional N-terminal, C-terminal, or intermediate amino acid sequences, e.g., linkers or tags. "Linker", as used herein, is an amino acid sequences or insertion that can be used to connect or separate two distinct polypeptides or polypeptide fragments, wherein the linker does not otherwise contribute to the essential function of the composition. A polypeptide provided herein, can have an amino acid linker comprising, for example, the amino acids GLS, ALS, or LLA. A "tag", as used herein, refers to a distinct amino acid sequence that can be used to detect or purify the provided polypeptide, wherein the tag does not otherwise contribute to the essential function of the composition. The provided polypeptide can further have deleted N-terminal, C-terminal or intermediate amino acids that do not contribute to the essential activity of the polypeptide.

The disclosed composition can be linked to an internalization sequence or a protein transduction domain to effectively enter the cell. Recent studies have identified several cell penetrating peptides, including the TAT transactivation domain of the HIV virus, antennapedia, and transportan that can readily transport molecules and small peptides across the plasma membrane (Schwarze et al., 1999; Derossi et al., 1996; Yuan et al., 2002). More recently, polyarginine has shown an even greater efficiency of transporting peptides and proteins across the plasma, membrane making it an attractive tool for peptide mediated transport (Fuchs and Raines, 2004). Non-arginine ($R_9$, SEQ ID NO:18) has been described as one of the most efficient polyarginine based protein transduction domains, with maximal uptake of significantly greater than TAT or antennapeadia. Peptide mediated cytotoxicity has also been shown to be less with polyarginine-based INernalization sequences. $R_9$ mediated membrane transport is facilitated through heparan sulfate proteoglycan binding and endocytic packaging. Once internalized, heparan is degraded by heparanases, releasing $R_9$ which leaks into the cytoplasm (Deshayes et al., 2005). Studies have recently shown that derivatives of polyarginine can deliver a full length p53 protein to oral cancer cells, suppressing their growth and metastasis, defining polyarginine as a potent cell penetrating peptide (Takenobu et al., 2002).

Thus, the provided polypeptide can comprise a cellular internalization transporter or sequence. The cellular internalization sequence can be any internalization sequence known or newly discovered in the art, or conservative variants thereof. Non-limiting examples of cellular internalization transporters and sequences include Polyarginine (e.g., $R_9$), Antennapedia sequences, TAT, HIV-Tat, Penetratin, Antp-3A (Antp mutant), Buforin II, Transportan, MAP (model amphipathic peptide), K-FGF, Ku70, Prion, pVEC, Pep-1, SynB1, Pep-7, HN-1, BGSC (Bis-Guanidinium-Spermidine-Cholesterol, and BGTC (Bis-Guanidinium-Tren-Cholesterol).

Any other internalization sequences now known or later identified can be combined with a peptide of the invention.

3. Protein Variants

Protein variants and derivatives are well understood to those of skill in the art and in can involve amino acid sequence modifications. For example, amino acid sequence modifications typically fall into one or more of three classes: substitutional, insertional or deletional variants. Insertions include amino and/or carboxyl terminal fusions as well as Intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place.

Substantial changes in function or immunological identity are made by selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and aspartyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

It is understood that one way to define the variants and derivatives of the disclosed proteins herein is through defining the variants and derivatives in terms of homology/identity to specific known sequences. Specifically disclosed are variants of these and other proteins herein disclosed which have at least, 70% or 75% or 80% or 85% or 90% or 95% homology to the stated sequence. Those of skill in the art readily understand how to determine the homology of two proteins. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. Mol. Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. Science 244:48-52, 1989, Jaeger et al. Proc. Natl. Acad. Sci. USA 86:7706-7710, 1989, Jaeger et al. Methods Enzymol. 183:281-306, 1989 which are herein incorporated by reference for at least material related to nucleic acid alignment.

It is understood that the description of conservative mutations and homology can be combined together in any combination, such as embodiments that have at least 70% homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence.

It is understood that there are numerous amino acid and peptide analogs which can be incorporated into the disclosed compositions. For example, there are numerous D amino acids or amino acids which have a different functional substituent then the amino acids shown in Table 1 and Table 2. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way (Thorson et al., Methods in Molec. Biol. 77:43-73 (1991), Zoller, Current Opinion in Biotechnology, 3:348-354 (1992); Ibba, Biotechnology & Genetic Engineering Reviews 13:197-216 (1995), Cahill et al., TIBS, 14(10):400-403 (1989); Benner, TIB Tech, 12:158-163 (1994); Ibba and Hennecke, Bio/technology, 12:678-682 (1994) all of which are herein incorporated by reference at least for material related to amino acid analogs).

Molecules can be produced that resemble peptides, but which are not connected via a natural peptide linkage. For example, linkages for amino acids or amino acid analogs can include CH₂NH—, —CH₂S—, —CH₂—CH₂—, —CH=CH—(cis and trans), —COCH₂—, —CH(OH) CH₂—, and —CHH₂SO—. (These and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci (1980) pp. 463-468; Hudson, D. et al., IN J Pept Prot Res 14:177-185 (1979) (—CH₂NH—, CH₂CH₂—); Spatola et al. Life Sci 38:1243-1249 (1986) (—CH H₂—S); Hann J. Chem. Soc Perkin Trans. I 307-314 (1982) (—CH—CH—, cis and trans); Almquist et al. J. Med. Chem. 23:1392-1398 (1980) (—COCH₂—); Jennings-White et al. Tetrahedron Lett 23:2533 (1982) (—COCH₂—); Szelke et al. European Appln, EP 45665 CA (1982): 97:39405 (1982) (—CH(OH)CH₂—); Holladay et al. Tetrahedron. Lett 24:4401-4404 (1983) (—C (OH)CH₂—); and Hruby Life Sci 31:189-199 (1982) (—CH₂—S—); each of which is incorporated herein by reference. A particularly preferred non-peptide linkage is —CH₂NH—. It is understood that peptide analogs can have more than one atom between the bond atoms, such as b-alanine, g-aminobutyric acid, and the like.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. (Rizo and Gierasch Ann. Rev. Biochem. 61:387 (1992), incorporated herein by reference).

B. Methods of Use

1. Inhibiting Viral Integrase

Described herein are methods of reducing or inhibiting viral integrase activity by contacting a viral integrase with a peptide disclosed herein. In some aspects, the viral integrase is HIV integrase.

Without wishing to be bound by theory, in some aspects, the peptide can bind to viral integrase such as, for example, HIV IN, and inhibit strand transfer complex (STC) formation and subsequent viral DNA integration. Alternatively, the peptide allows for STC formation but blocks subsequent viral DNA integration.

In some aspects, the method comprises contacting HIV IN with a peptide disclosed herein. For example, the method can comprise contacting HIV IN with a peptide comprising SEQ ID NO:1, SEQ ID NO:2, SEQ ID NO:3, or SEQ ID NO:4. In some aspects, the peptide is a conservative variant of SEQ ID NO:1, SEQ ID NO:2, SEQ ID NO:3, or SEQ ID NO:4. In some aspects, the peptide has an amino acid sequence that is at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% homologic to SEQ ID NO:1, SEQ ID NO:2, or SEQ ID NO:3, or SEQ ID NO:4.

In some aspects, the peptide is a fusion protein comprising a first amino acid sequence that targets the integrase and a second amino acid sequence. For example, the second amino acid sequence can comprise an internalization sequence or tag.

The peptide can be an endogenous, an isolated, or a synthetically derived peptide. For example, the peptide may be directly chemically synthesized. In another aspect, a nucleic acid sequence encoding the peptide may be incorporated into a vector and expressed within, for example, bacteria and subsequently purified.

In some aspects, the nucleic acid sequence encoding the peptide can be readily modified to create a nucleic acid fusion gene which would encode a fusion peptide. This recombinant peptide may include epitopes or tags such as a glutathione S-transferase (GST) tag, a myc tag, a FLAG tag, or a 6-His tag to further aid in peptide isolation and purification steps. Purification or isolation steps may include numerous techniques known in the art such as "salting out" the peptide, using sucrose gradient centrifugation, or chromatography steps including size exclusion chromatography, ion exchange chromatography, immunoaffinity chromatography, HPLC, or affinity chromatography to further isolate the peptide. In one aspect, the peptide having an epitope or tag may be cleaved or removed after isolation of the peptide. In another aspect, the epitope or tag is not cleaved or removed after isolation.

2. Treating HIV

Also disclosed is a method of treating or preventing HIV in a subject, comprising administering to the subject a peptide disclosed herein. For example, the method can comprise administering to the subject a peptide comprising SEQ ID NO:1, SEQ ID NO:2, SEQ ID NO:3, or SEQ ID NO:4. In some aspects, the method comprises administering to the subject a conservative variant of SEQ ID NO:1, SEQ ID NO:2, SEQ ID NO:3, or SEQ ID NO:4. In some aspects, the method can comprise administering to the subject an amino acid sequence that is at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% homologic to SEQ ID NO:1, SEQ ID NO:2, or SEQ ID NO:3, or SEQ ID NO:4.

In some aspects, the subject is at risk for HIV infection. In some aspects, the subject has HIV.

In some aspects, the peptide can be modified to enhance administration to a subject, tissues, or cells. In this aspect, the peptide can be combined or complexed with a polymeric material to enhance administration to a subject, tissues, or cells. In yet another aspect, the peptide can be covalently linked to or genetically engineered to have a cellular Internalization sequence or protein transduction domain including HIV-1 TAT, HSV VP22, or Antp, to further enhance administration to a subject, tissues, or cells.

These compositions can be administered orally in the form of a capsule, a vaccine administered intravenously, subcutaneously, or intramuscularly, an intravenous drip, or a transdermal, topical cream. Examples of the polymeric material to which the peptide, small molecule, or any combination thereof may be complexed includes amphiphilic polymers, hydrophilic polymers, hydrophobic polymers, nanoparticles, micelles, immunoconjugates, dendrimers and liposomes. Without wishing to be bound by theory, the peptide, the small molecule, or any combination thereof may be conjugated or complexed with one of the polymers mentioned above using Particle Replication In Non-wetting Templates (PRIN). PRIN allows for the elucidation of mechanisms by which organic particles of controlled size, shape, site-specific surface chemistry, tunable particle matrix composition and tunable modulus undergo endocytosis. Obtaining knowledge of endocytic pathways used from "calibration quality" particles should lead to crucial information required for not only enhancing specific cellular internalization, but also manipulating the intracellular location of particles, and minimizing cytotoxic effects. Once the mechanisms of internalization are established, it is then possible to use these findings to better engineer the intracellular release of specific cargos.

The complexes described above can be administered to a subject using techniques known in the art. For example, pharmaceutical compositions can be prepared with the complexes. It will be appreciated that the actual preferred amounts of the complex in a specified case will vary according to the specific compound being utilized, the particular compositions formulated, the mode of application, and the particular situs and subject being treated. Dosages for a given host can be determined using conventional considerations, e.g., by customary comparison of the differential activities of the subject compounds and of a known agent, e.g., by means of an appropriate conventional pharmacological protocol. Physicians and formulators, skilled in the art of determining doses of pharmaceutical compounds, will have no problems determining dose according to standard recommendations (Physicians Desk Reference, Barnhart Publishing (1999).

Pharmaceutical compositions described herein can be formulated in any excipients the biological system or entity can tolerate. Examples of such excipients include, but are not limited to, water, saline, Ringer's solution, dextrose solution, Hank's solution, and other aqueous physiologically balanced salt solutions. Nonaqueous vehicles, such as fixed oils, vegetable oils such as olive oil and sesame oil, triglycerides, propylene glycol, polyethylene glycol, and injectable organic esters such as ethyl oleate can also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosol, cresols, formalin and benzyl alcohol.

Pharmaceutical carriers are known to those skilled in the art. These most typically would be standard carriers for administration to humans, including solutions such as sterile water, saline, and buffered solutions at physiological pH.

Molecules intended for pharmaceutical delivery can be formulated in a pharmaceutical composition. Pharmaceutical compositions can include carriers, thickeners, diluents, buffers, preservatives, surface active agents and the like in addition to the molecule of choice.

The pharmaceutical composition can be administered in a number of ways depending on whether local or systemic treatment is desired, and on the area to be treated. Administration can be topical, including ophthalmic and intranasal, or administration may be intravenous or intraperitoneal.

Preparations for administration include sterile aqueous or non-aqueous solutions, suspensions, and emulsions. Examples of non-aqueous carriers include water, alcoholic/aqueous solutions, emulsions or suspensions, including saline and buffered media. Parenteral vehicles, if needed for collateral use of the disclosed compositions and methods, include sodium chloride solution, Ringer's dextrose, dextrose and sodium chloride, lactated Ringer's, or fixed oils, intravenous vehicles, if needed for collateral use of the disclosed compositions and methods, include fluid and nutrient replenishers, electrolyte replenishers (such as those based on Ringer's dextrose), and the like. Preservatives and other additives can also be present such as, for example, antimicrobials, anti-oxidants, chelating agents, and inert gases and the like.

Formulations for topical administration can include ointments, lotions, creams, gels, drops, suppositories, sprays, liquids and powders. Conventional pharmaceutical carriers, aqueous, powder or oily bases, thickeners and the like can be necessary or desirable.

In one aspect, the peptide including SEQ ID NO:1, SEQ ID NO:2, SEQ ID NO:3, SEQ ID NO:4, any variant thereof, small molecule, or any combination thereof may be administered to a subject at risk for HIV infection. In another aspect, the peptide including SEQ ID NO:1, SEQ ID NO:2, SEQ ID NO:3, SEQ ID NO:4, any variant thereof, small molecule, or any combination thereof may be administered to a subject having HIV. Upon administration to the subject, the peptide including SEQ ID NO:1, SEQ ID NO:2, SEQ ID NO:3, SEQ ID NO:4, any variant thereof, small molecule, or any combination thereof binds to HIV IN and either reduces, inhibits, or sequentially reduces and then inhibits HIV IN activity and viral DNA integration.

The disclosed compounds and compositions can be administered in any suitable manner. The manner of administration can be chosen based on, for example, whether local or systemic treatment is desired, and on the area to be treated. For example, the compositions can be administered orally, parenterally (e.g., intravenous, subcutaneous, intraperitoneal, or intramuscular injection), by inhalation, extracorporeally, topically (including transdermally, ophthalmically, vaginally, rectally, intranasally) or the like.

As used herein, "topical intranasal administration" means delivery of the compositions into the nose and nasal passages through one or both of the areas and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via incubation.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The exact amount of the compositions required can vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein. Thus, effective dosages and schedules for administering the compositions may be determined empirically, and making such determinations is within the skill in the art. The dosage ranges for the administration of the compositions are those large enough to produce the desired effect in which the symptoms of disorder are affected. The dosage should not be so large as to cause adverse side effects, such as unwanted cross-reactions, anaphylactic reactions, and the like. Generally, the dosage can vary with the age, condition, sex and extent of the disease in the patient, route of administration, or whether other drugs are included in the regimen, and can be determined by one of skill in the art. Dosage can vary, and can be administered in one or more dose administrations daily, for one or several days. Guidance can be found in the literature for appropriate dosages for given classes of pharmaceutical products.

Dosing is dependent on severity and responsiveness of the condition to be treated, but will normally be one or more doses per day, with course of treatment lasting from several days to several months or until one of ordinary skill in the art determines the delivery should cease. Persons of ordinary skill can easily determine optimum dosages, dosing methodologies and repetition rates. For example, a typical daily dosage used alone might range from about 1 µg/kg to up to 100 mg/kg of body weight or more per day, depending on the factors mentioned above.

In one aspect, to find optimal concentrations for administration of the peptide, small molecule or any combination thereof to cells, tissues, or to a subject, dose-response curves may be generated and half maximal inhibitory concentration ($IC_{50}$) and median lethal dose ($LD_{50}$) may be measured. Concentrations may be further optimized based off of these measurements to administer the peptides, the small molecules, or any combination thereof to cells, tissues, or to a subject. In this aspect, the peptide, small molecule, or any combination thereof may include a therapeutic concentration including 1 µM, 2 µM, 3 µM, 4 µM, 5 µM, 6 µM, 7 µM, 8 µM, 9 µM, 10 µM, 11 µM, 12 µM, 13 µM, 14 µM, 15 µM, 16 µM, 17 µM, 18 µM, 19 µM, 20 µM, 21 µM, 22 µM, 23 µM, 24 µM, 25 µM, 26 µM, 27 µM, 28 µM, 29 µM, 30 µM, 31 µM, 32 µM, 33 µM, 34 µM, 35 µM, 36 µM, 37 µM, 38 µM, 39 µM, 40 µM, 41 µM, 42 µM, 43 µM, 44 µM, 45 µM, 46 µM, 47 µM, 48 µM, 49 µM, 50 µM, 51 µM, 52 µM, 53 µM, 54 µM, 55 µM, 56 µM, 57 µM, 58 µM, 59 µM, 60 µM, 61 µM, 62 µM, 63 µM, 64 µM, 65 µM, 66 µM, 67 µM, 68 µM, 69 µM, 70 µM, 71 µM, 72 µM, 73 µM, 74 µM, 75 µM, 76 µM, 77 µM, 78 µM, 78 µM, 79 µM, 80 µM, 81 µM, 82 µM, 83 µM, 84 µM, 85 µM, 86 µM, 87 µM, 88 µM, 89 µM, 90 µM, 91 µM, 92 µM, 93 µM, 94 µM, 95 µM, 96 µM, 97 µM, 98 µM, 99 µM, and 100 µM. Also in this aspect, therapeutic concentrations may range from 1 to 1000 µM, from 50 to 800 µM, from 100 to 600 µM, from 200 to 400 µM, or any combination thereof. In another aspect, the peptide, small molecules, or any combination thereof may include a therapeutic concentration within the submicromolar range including 1 to 1000 nM, 50 to 900 nM, 100 to 850 nM, 150 to 800 nM, 200 to 750 nM, 250 to 700 nM, 300 to 650 nM, 350 to 600 nM, 400 to 550 nM, 450 to 500 nM, or any combination thereof.

The compositions that inhibit HIV IN disclosed herein may be administered prophylactically to patients or subjects who are at risk for HIV or who have been newly diagnosed with HIV.

3. Screening for Viral Integrase Inhibitors

Also provided herein is a method of identifying an agent that reduces HIV integrase activity. In some aspects, this method comprises identifying an agent that inhibits HIV IN. In some aspects, this method can be used to identify an agent that can be used to treat HIV.

Thus, also provided herein is a method of identifying an agent that inhibits HIV IN, comprising providing a sample comprising at least one domain of the HIV IN and a peptide disclosed herein under conditions that allow binding of the HIV IN and the peptide, contacting the sample with a candidate agent, detecting the level of HIV IN/peptide binding, comparing the binding level to a control, a decrease in HIV IN/peptide binding compared to the control identifying an agent that can be used to treat a patient.

In some aspects, the at least one domain of the HIV IN comprises the N-terminus or C-terminus. In some aspects, the at least one domain of the HIV IN comprises the core domain between 48-210 a.a. Also disclosed is a method of identifying an agent that inhibits HIV IN, comprising contacting at least one domain of HIV IN with a candidate agent and measuring the integrase activity. In some aspects, the method comprises comparing the HIV integrase activity to a positive and a negative control.

Also disclosed is a method of identifying a candidate agent that reduces viral integrase activity comprising contacting at least one domain of the integrase with a peptide disclosed herein under conditions that allow the binding of the peptide to the integrase, contacting the integrase with a candidate agent, and determining whether the candidate agent displaced the peptide.

Thus, also disclosed is a method of identifying a candidate agent that reduces HIV integrase activity comprising contacting at least one domain of the HIV integrase with a peptide having at least 90% sequence identity to SEQ ID NO:1, SEQ ID NO:2, SEQ ID NO:3, or SEQ ID NO:4 under conditions that allow the binding of the peptide to the integrase, contacting the HIV integrase with a candidate agent, and determining whether the candidate agent displaced the peptide, wherein displacement of the peptide is an indication that the candidate agent reduces HIV integrase activity.

In some aspects, the method further comprises contacting a sample comprising the integrase with a candidate agent that displaced the peptide and measuring integrase activity to verify the ability of the candidate agent to inhibit the integrase. In some aspects, the integrase activity is measured using a DNA integration assay, southern blotting, western blotting, a high-throughput screening assay, or any combination thereof.

The binding of the peptides disclosed herein to an integrase, such as HIV IN, can be detected using routine methods, such as immunodetection methods, that do not disturb protein binding. The methods can be cell-based or cell-free assays. The steps of various useful immunodetection methods have been described in the scientific literature, such as, e.g., Maggio et al., Enzyme-Immunoassay, (1987) and Nakamura, et al., Enzyme Immunoassays: Heterogeneous and Homogeneous Systems, Handbook of Experimental Immunology, Vol. 1: Immunochemistry, 27.1-27.20 (1986), each of which is incorporated herein by reference in its entirety and specifically for its teaching regarding immunodetection methods. Immunoassays, in their most simple and direct sense, are binding assays involving binding between antibodies and antigen. Many types and formats of immunoassays are known and all are suitable for detecting the disclosed biomarkers. Examples of immunoassays are enzyme linked immunosorbent assays (ELISAs), radioimmunoassays (RIA), radioimmune precipitation assays (RIPA), immunobead capture assays, Western blotting, dot blotting, gel-shift assays, Flow cytometry, protein arrays, multiplexed bead arrays, magnetic capture, in vivo imaging, fluorescence resonance energy transfer (FRET), and fluorescence recovery/localization after photobleaching (FRAP/FLAP).

In some aspects, the candidate agent can be identified using a yeast two-hybrid system or similar cell-based reporter assay. In these aspects, transcriptional activation in the yeast can be an indication that the peptide is binding the HIV integrase. For example, in one aspect, at least one domain of HIV integrase includes a bait fused to a DNA binding domain. The domain may include the N-terminus, central core, or C-terminus of HIV IN. For example, the C-terminus of HIV IN can be fused to the GAL4 DNA binding domain. In this aspect, a peptide that binds HIV IN disclosed herein can be used as a prey fused to an activation domain. For example, the peptide can be fused to the GAL4 activation domain. In some aspects, a peptide comprising the amino acid sequence SEQ ID NO:1, SEQ ID NO:2, SEQ ID NO:3, SEQ ID NO:4, or any combination thereof can be fused to the GAL4 activation domain. In some aspects, if the bait and prey interact, a reporter gene such as HIS3, URA3, ADE3, Zsgreen, GFP, beta-galactosidase, or luciferase, can be transcribed and subsequently translated. Depending on reporter gene expression, the strength of the bait and prey interaction can be further analyzed. One of ordinary skill in the art can readily modify this assay to allow for a bait comprising a peptide fused to a DNA binding domain and to allow for a prey comprising at least one domain of HIV integrase fused to an activation domain. One of ordinary skill in the art would readily appreciate additional constructs, binding domains, activation domains, and reporter genes including green fluorescent protein may be readily substituted for those listed above.

In some aspects, the candidate agent displaces the peptide from the HIV IN. Thus, the method can comprise detecting the binding of the peptide to the integrase. In some aspects, the method comprises detecting peptide displaced from the integrase. In this aspect, when using the yeast two hybrid screen described above, reporter gene expression will be observed if using SEQ ID NO:1, SEQ ID NO:2, SEQ ID NO:3, or SEQ ID NO:4.

To screen chemical libraries for inhibitors of HIV IN, the actual binding of the chemical to a portion or domain of HIV IN may be assayed. In one aspect, a small molecule from a chemical library may be added to the yeast two hybrid systems mentioned above. Without wishing to be bound by theory, if the chemical has equal or greater affinity for the viral integrase than the peptide's affinity for the viral integrase, the peptide will be displaced. Upon being displaced, expression of the reporter gene will decrease or be completely inhibited. This result would indicate chemical binding to the viral integrase, and it would provide a qualitative and quantitative measure of the chemical's binding affinity to the viral integrase.

In another aspect, this assay may be varied to allow for a competition-type assay in which the chemical or small molecule and the prey are added in a specific amount simultaneously or at least in close time proximity. Depending on the affinity to the prey, either the chemical/small molecule or the prey will out-compete the other and the chemical/small molecule's affinity for viral integrase or a viral integrase domain may be determined qualitatively, quantitatively, or any combination thereof.

In another aspect, these yeast two hybrid systems can be adapted for high-throughput screening. For example, cells may be grown in a 96-well format 1530 or up to a 16640 well format and dispensed with a plate filler. Using this format, at least 5,000, 10,000, 20,000, 30,000, 40,000, 50,000, 60,000, 70,000, 80,000, 90,000, or 100,000 assays may be conducted every two weeks. In one aspect, a yeast screening robot is used and a lab information management system (LIMS) tracks samples and handles data. The LIMS incorporates bar coding, process records, and quality controls within the framework of an oracle database. A range of chemical and peptide concentrations may be tested as stated above. In this aspect, true positives will be selected for interaction by the peptide or small molecule with HIV integrase and for optimal concentration. True positives may be recovered at a rate of ~1% and the frequency of large negative effects on yeast growth is low (<10%). Positives (defined as signal >2-3 SD below the mean signal) may be rescreened, and for the active subset, dose/response studies may be conducted. Positives may be evaluated further in mammalian bioassays, and biased libraries may be developed to identify chemicals or small molecules with stronger, more selective effects for HIV integrase.

To further analyze the enzymatic reduction or inhibition of viral integrase, viral DNA integration and STC formation and accumulation may be assayed. In one aspect, a DNA integration assay, Southern blotting, Western blotting, a high-through put screening assay modified to measure integrase activity (John, et al. Development and Application of a High-Throughput Screening Assay for HIV-1 Integrase Enzyme Activities. J. of Biomolecular Screening. (2005) 10(6): 606-614 is hereby incorporated by reference in its entirety), or any combination thereof may be used to analyze a reduction or inhibition of viral integrase activity. These assays may be further used to analyze strand transfer complex (STC) formation and possible accumulation. For example, a DNA integration assay, as described within Craigie, et al. Processing of viral DNA ends channels the HIV-1 integration reaction to concerted integration. *J. Biol. Chem.* (2005) 280(32):29334-9 and Craigie, et al. Retroviral DNA integration: reaction pathway and critical intermediates. *EMBO J.* (2006) 25(6):1295-304 and which are hereby incorporated by reference in their entirety, may be used to determine whether a peptide, small molecule, or any combination thereof inhibits viral DNA integration. In a further aspect, viral DNA integration of a cell, tissue, or subject contacted or administered with a peptide including SEQ ID NO:1, SEQ ID NO:2, SEQ ID NO:3, SEQ ID NO:4 or any variant thereof, small molecule, or any combination thereof may be compared to positive and negative controls to provide a qualitative and quantitative measurement of the reduction or inhibition of viral integrase activity.

a. HIV Integrase Mutants

Drugs that block the enzymatic function of HIV IN can prevent the integration of the virus into the genome. Raltegravir, also known as Isentress or MK0518, made by Merck has been FDA approved for use in patients that are resistant to other drugs. Other IN inhibitors include diketo analogues (DKA) S-1360, L-870, 810, Elvitegravir (GS-9137), and Naphthyridinone GSK364735. Although Raltegravir shows remarkable benefits, mutations in the gene encoding HIV IN lead to viral mutants resistant to the drug. In some studies, failure rates due to resistance to MK0518 and GS-9137 have reached 25% and 40%, respectively. integrase mutations to inhibitors include Q148R, N155H, L74M, E92Q, as well as, other amino acids. Some amino acids changes that lead to resistance to IN inhibitors have been shown to directly interact with the IN inhibitor 5CITEP.

Thus, in some aspects of the disclosed screening methods, at least one domain of HIV integrase comprises a drug resistant mutation. For example, the drug resistant mutation can be T66I, T66A, T66K, E92Q, F121Y, E138A, E138K, G140A, G140S, Y143R, Y143C, Y143H, S147G, Q148H, Q148R, Q148K, S153Y, N155H, N155S, R263K, L74M, E92Q, T97A, V151I, E157Q, G163R, I203M, S230R, S230N, H51Y, Q95K, H114Y, P145S, Q146P, T125K, A128T, Q146K, N155S, K160D, V72I, A154I, V165I and V201I (http://hivdb.stanford.edu/cgi-bin/INIResiNote.cgi), or any combination thereof.

Thus, also disclosed herein is a method of identifying a candidate agent that inhibits an HIV IN mutant in addition to or instead of wild type HIV IN. In some aspects, the method comprises first identifying peptides that bind the mutant HIV IN. One way to identify peptides that bind mutant HIV IN is to prepare and examine peptides that are mutants of the peptides of SEQ ID NO:1, SEQ ID NO:2, SEQ ID NO:3, SEQ ID NO:4 or any variant thereof that bind wild type HIV IN (referred to herein as "mutated binding peptides"). For example, the mutated-binding peptides can have at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence homology to SEQ ID NO:1, SEQ ID NO:2, SEQ ID NO:3, SEQ ID NO:4 or any variant thereof. Thus, the mutated-binding peptides can be produced using random mutagenesis, degenerate oligonucleotides, DNA shuffling, site-directed mutagenesis, or any other method available in the art suitable for creating a peptide library containing peptides within the desired sequence identity.

Thus, also disclosed is a method of identifying a candidate agent that reduces viral integrase activity comprising contacting at least one domain of a mutant integrase with a mutant-binding peptide disclosed herein under conditions that allow the binding of the peptide to the mutant integrase, contacting the mutant integrase with a candidate agent, determining whether the candidate agent displaced the mutant-binding peptide.

In some aspects, the mutant-binding peptides can bind one or more mutant or wild type HIV IN. Thus, the method can also comprise testing the binding ability of any agent to a mutant IN to mutant wild type HIV IN and/or other mutant HIV INs. Allele-specific suppression has been used extensively as a genetic tool for the identification and analysis of physical interactions involving RNA, DNA, and protein (Hartman and Roth, 17:1-105 Adv. Genetics (1973); Nelson and Sauer, Cell 42:549-558 (1985); Betz, J. Mol. Biol. 195: 495-504 (1987); Adams et al., Genetics 121:675-683 (1989); Parker, Methods Enzymol. 180:510-517 (1989); Mortin, Proc. Natl. Acad. Sci. USA 87:4864-4868 (1990); Oertel-Buchheit et al., J. Mol. Biol., 255:609-620 (1992); Phizicky and Fields, Microbiol. Rev. 59:94-123 (1995). A widely held view of the mechanism by which allele-specific suppression occurs invokes the "lock-and-key" model, in which the original contact is restored. In the case of RNA-RNA interactions, where interactions can be restored by mutations that allow compensatory changes in base-pairing. Allele-specific suppression is often taken as evidence of protein-protein interactions; conversely non-allele specific suppression is usually taken as evidence of bypass suppression.

The principle of allele-specific suppression is applied in the present invention to detect integrase interactions. Thus, also disclosed is a yeast genetic method of identifying a candidate agent that inhibits activity of a mutated HIV integrase. If a mutant integrase decreases the interaction of a wild type IN binding peptide, such as peptide SEQ ID NO:1, SEQ ID NO:2, SEQ ID NO:3, SEQ ID NO:4 or any variant thereof, with the mutant integrase, the mutant suppressing peptides can be selected which recovers the binding/inhibition of the mutant integrase. Wild type integrase can be linked to a DNA binding domain and the peptide to an activation domain or the reverse. When DB-integrase bound to the operator of a selectable reporter (e.g. LEU2, URA3, HIS3, ADE2) interacts with the peptide linked to the activation, the reporter is activated allowing growth on media lacking the amino-acid encoded by the reporter. In the case of HIS3, the stringency can be strengthened by the addition of 3-AT. To select for natural mutations, millions of yeast can be screened by plating the strain on synthetic plates lacking histidine with added 3-AT (3-amino triazole). Plasmids from colonies that grow on the selection media can be isolated and retransformed into the base strain to check for plasmid linkage. Clones that pass plasmid linkage analysis would be sequenced to identify mutation in the DNA region encoding the peptide that recapitulates the interaction with the mutant integrase. The peptide mutants can be tested with the wild-type integrase as well as other mutant integrase alleles. All different classes of mutations are possible, allele-specific mutations, general increases in affinity or mutants that bind to a different region of integrase. Alternatively, the region encoding the peptide can also be mutated using degenerate oligos, primers or split ligation (random DNA oligo). Once finding a peptide that binds to the mutated integrase, it can be used to screen for chemicals that displace the peptide as described above.

Integrase mutants that are resistant to the peptide of SEQ ID NO:1, SEQ ID NO:2, SEQ ID NO:3, SEQ ID NO:4 or any variant thereof can be identified using a yeast genetic approach. To screen for mutants in integrase that result in loss of binding to the peptide SEQ ID NO:1, SEQ ID NO:2, SEQ ID NO:3, SEQ ID NO:4 or any variant thereof. A strain containing the DNA binding (DB)-peptide and Activation domain (AC)-integrase driving a URA3 reporter could be plated onto 5-fluorooctane acid (5-FOA) plates. In the presence of 5-fluorooctane acid (5-FOA) in the growth media, cells expressing orotidine 5-phosphate decarboxylase will die due to convertion of 5-FOA into 5-fluorouracil, a toxic compound. (Boeke J D et al., Methods Enzymol. 154:164-75 (1987). 5-FOA is an extremely useful reagent for the selection of Ura− cells amid a population of Ura+ cells. The selection is effective in transformation and recombination studies where loss of URA3+ is desired.

Other aspects include applications of variation on the theme disclosed above with the use of drugs that block the interaction between the peptide and integrase.

Integrase activity assays in yeast: HIV-1 IN expressed as the sole retroviral protein in eukaryotic cells was sufficient to catalyze the complete integration of a DNA containing two viral LTRs into the nuclear genome.

b. Other Retrovirus

Numerous examples exist of proteins binding across evolutionary species. Yeast and vertebrate fimbrins are similar in both primary structure and biochemical activities. Human T- and L fimbrins, can complement the sac6 null defect in the yeast *S. cerevisiae* (Adams et al., Molecular and Cellular Biology 15(1):69-75 (1995)). The central region (located between residues 50 and 212) contains a triad of three invariant acidic residues (Asp64, Asp116 and Glu152), commonly called the D,D-35-E domain, which are evolutionarily highly conserved among retroviral IN proteins as well as various eukaryotic and prokaryotic transposases (Kulkosky et al., Molecular Cell Biology 12: 2331-2338 (1992); Doak et al., Proc. Natl. Acad. Sci. 91:942-946 (1994); Rice and Mizuuchi, Cell 82:209-220 (1995)).

A retrovirus is an RNA virus that is replicated in a host cell via the enzyme reverse transcriptase to produce DNA from its RNA genome. The DNA is then incorporated into the host's genome by an integrase enzyme. The virus thereafter replicates as part of the host cell's DNA. Retroviruses are enveloped viruses that belong to the viral family Retroviridae. The virus classification is Group VI. Two Genera subfamilies include Orthoretrovirinae and Supumaretrovirinae. The subfamilies include Alpharetrovirus (Avian Sarcoma Leukosis Virus, Rous sarcoma virus), Betaretovirus (Mouse mammary tumor virus), Gammaretrovirus (Murine leukemia virus, Abelson murine leukemia virus, Feline leukemia virus, Xenotropic murine leukemia virus-related virus), Deltaretrovirus (Human T-lymphotropic virus (HTLV-1, HTLV-2) Bovine leukemia virus, Epsilonretrovirus (Walleye epidermal hyperplasia virus), and Lentivirus (Human immunodeficiency virus, Simian immunodeficiency virus, Feline leukemia virus, Puma lentivirus, EIA, Bovine immunodeficiency virus, Caprine arthritis encephalitis virus, Visna/maedi virus). A second subfamily includes Spumaretrovirinae (Simian foamy virus and HFV).

Therefore, other embodiments of the present invention include using the peptides of SEQ ID NO:1, SEQ ID NO:2, SEQ ID NO:3, SEQ ID NO:4 or any variant thereof as probes to select for inhibitors for other retrovirus integrases. For example, the viral integrase encoded by any of these retrovirus could be cloned into the two hybrid system and tested for interaction with the peptide of SEQ ID NO:1, SEQ ID NO:2, SEQ ID NO:3, SEQ ID NO:4 or any variant thereof. When an interaction is detected, agents can be directly selected that bind to the other retroviral integrases as described above. The peptide could be mutated as described with mutated HIV integrases to select for interaction with the other retrovirus integrases. Three dimensional structural information can also be employed to design peptides that bind to other evolutional conserved integrases.

c. Candidate Agents

In general, candidate agents can be identified from large libraries of natural products or synthetic (or semi-synthetic) extracts or chemical libraries according to methods known in the art. Those skilled in the field of drug discovery and development will understand that the precise source of test extracts or compounds is not critical to the screening procedure(s) of the invention. Accordingly, virtually any number of chemical extracts or compounds can be screened using the exemplary methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, polypeptide- and nucleic acid-based compounds. Synthetic compound libraries are commercially available, e.g., from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Furthermore, if desired, any library or compound is readily modified using standard chemical, physical, or biochemical methods. In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their effect on the activity of HIV IN should be employed whenever possible.

When a crude extract is found to have a desired activity, further fractionation of the positive lead extract is necessary to isolate chemical constituents responsible for the observed effect. Thus, the goal of the extraction, fractionation, and purification process is the careful characterization and identification of a chemical entity within the crude extract having an activity that stimulates or inhibits HIV IN. The same assays described herein for the detection of activities in mixtures of compounds can be used to purify the active component and to test derivatives thereof. Methods of fractionation and purification of such heterogenous extracts are known in the art. If desired, compounds shown to be useful agents for treatment are chemically modified according to methods known in the art. Compounds identified as being of therapeutic value may be subsequently analyzed using animal models for diseases or conditions, such as those disclosed herein.

Candidate agents encompass numerous chemical classes, but are most often organic molecules, e.g., small organic compounds having a molecular weight of more than 100 and less than about 2,500 daltons. Candidate agents comprise functional groups necessary for structural interaction with proteins, particularly hydrogen bonding, and typically include at least an amine, carbonyl, hydroxyl or carboxyl group, for example, at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. In a further embodiment, candidate agents are peptides.

In some embodiments, the candidate agents are proteins. In some aspects, the candidate agents are naturally occurring proteins or fragments of naturally occurring proteins. Thus, for example, cellular extracts containing proteins, or random or directed digests of proteinaceous cellular extracts, can be used. In this way libraries of procaryotic and eucaryotic proteins can be made for screening using the methods herein. The libraries can be bacterial, fungal, viral, and vertebrate proteins, and human proteins.

C. Methods of Making the Compositions

The compositions disclosed herein and the compositions necessary to perform the disclosed methods can be made using any method known to those of skill in the art for that particular reagent or compound unless otherwise specifically noted.

1. Nucleic Acid Synthesis

For example, the nucleic acids, such as, the oligonucleotides to be used as primers can be made using standard chemical synthesis methods or can be produced using enzymatic methods or any other known method. Such methods can range from standard enzymatic digestion followed by nucleotide fragment isolation (see for example, Sambrook et al., Molecular Cloning: A Laboratory Manual, 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., Ann. Rev. Biochem. 53:323-356 (1984), (phosphotriester and phosphite-triester methods), and Narang et al., Methods Enzymol., 65:610-620 (1980), (phosphotriester method). Protein nucleic acid molecules can be made using known methods such as those described by Nielsen et al., Bioconjug. Chem. 5:3-7 (1994).

2. Peptide Synthesis

One method of producing the disclosed proteins, such as SEQ ID NO:1 to 4, is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. (Grant G A (1992) Synthetic Peptides: A User Guide. W.H. Freeman and Co., N.Y. (1992); Bodansky M and Trost B., Ed. (1993) Principles of Peptide Synthesis. Springer-Verlag Inc., NY (which is herein incorporated by reference at least for material related to peptide synthesis). Alternatively, the peptide or polypeptide is independently synthesized in vivo as described herein. Once isolated, these independent peptides or polypeptides may be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M et al. (1992) FEBS Lett. 307:97-101; Clark-Lewis I et al., J. Biol. Chem., 269: 16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992)).

D. Kits

The materials described above as well as other materials can be packaged together in any suitable combination as a kit useful for performing, or aiding in the performance of, the disclosed method. It is useful if the kit components in a given kit are designed and adapted for use together in the disclosed method. For example disclosed are kits for screening for HIV integrase inhibitors, the kit comprising one or more peptides disclosed herein and at lease one domain of HIV integrase. The kits also can contain one or more yeast two hybrid assay reagents. Also disclosed is a kit comprising one or more peptides disclosed herein as a library of potential integrase inhibitors.

E. Examples

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

Identification of Peptides that Interact with HIV IN

A yeast-based screening platform for identifying inhibitors of IN was constructed. In this platform, HIV IN was amplified from the pNL4-3 based provirus (R9) as template and cloned into two expression vectors resulting in a fusion of IN C-terminus to the GAL4 DNA binding domain (GALDB) and the GAL4 activation domain (GALAD) respectively. By western blot analysis, GALAD-IN was detected (not shown); however, GALDB-IN was barely detectable. Yeast harboring IN fused to the activation and binding domains activated the two-hybrid reporter, suggesting that sufficient amounts on IN were present to detect previously documented self-association. Other combinations of control vectors or HIV gag plus GALDB-IN or GALAD-IN failed to activate the reporter suggesting that viral integrase was not a self-activator.

To identify IN-binding peptides, yeast producing HIV integrase was mated with yeast harboring a random peptide library (15 amino acids in length; 27 million diverse) fused to the VP16 activation domain. Diploids were plated onto selection medium to identify clones that carry a peptide that has affinity to the viral target. Binders were confirmed by plasmid linkage analysis (FIG. 1). A single peptide, LeuTyrGluThrIleLeuIleLeuLeuPheLeuAspValAspThrGly (SEQ ID NO:1), emerged from the screen that interacted with the viral target but not false baits (HPVE6, and HPVE7). FIG. 1 shows interaction of a peptide with HIV IN by a two-hybrid. The peptide was cloned as a C-terminal fusion with VP16-Zsgreen and tested for interaction with the GALDB or GALDB-IN fusion in AH109 Mat a, trp1-901, leu2-3, 112, ura3-52, his3-200, gal4 Δ, gal 80Δ, LYS2::GAL1UAS-GAL1TATA-HIS3, GAL2UAS-GAL2TATA-ADE2, URA3:MEL1UAS-MEL1TATA-lacZ. Growth on -ade plates indicated activation of a selectable reporter. Addition of hydrophilic amino acids to the C-terminus allowed for a soluble peptide. A peptide having the sequence LeuTyrGluThrIleLeuIleLeuLeuPheLeuAspValAspThrGlyLysLysArg (SEQ ID NO:2) was synthesized and studied further. SEQ ID NO:2 has a basic tail (LysLysArg) which increased peptide solubility. Likewise, a peptide having the sequence LeuTyrGluThrIleLeuIleLeuLeuPheLeuAspValAspThrGly AspGluAsp (SEQ ID NO:3) was synthesized and studied further. SEQ ID NO:3 has an acidic tail (AspGluAsp) which increased peptide solubility.

Example 2

Confirmation of IN Inhibition

To confirm IN inhibition by SEQ ID NO:1, SEQ ID NO:2, and SEQ ID NO:3, a concerted integration assay test was used to measure the level of DNA integration by a construct mimicking a retrovirus.

Figure 2:
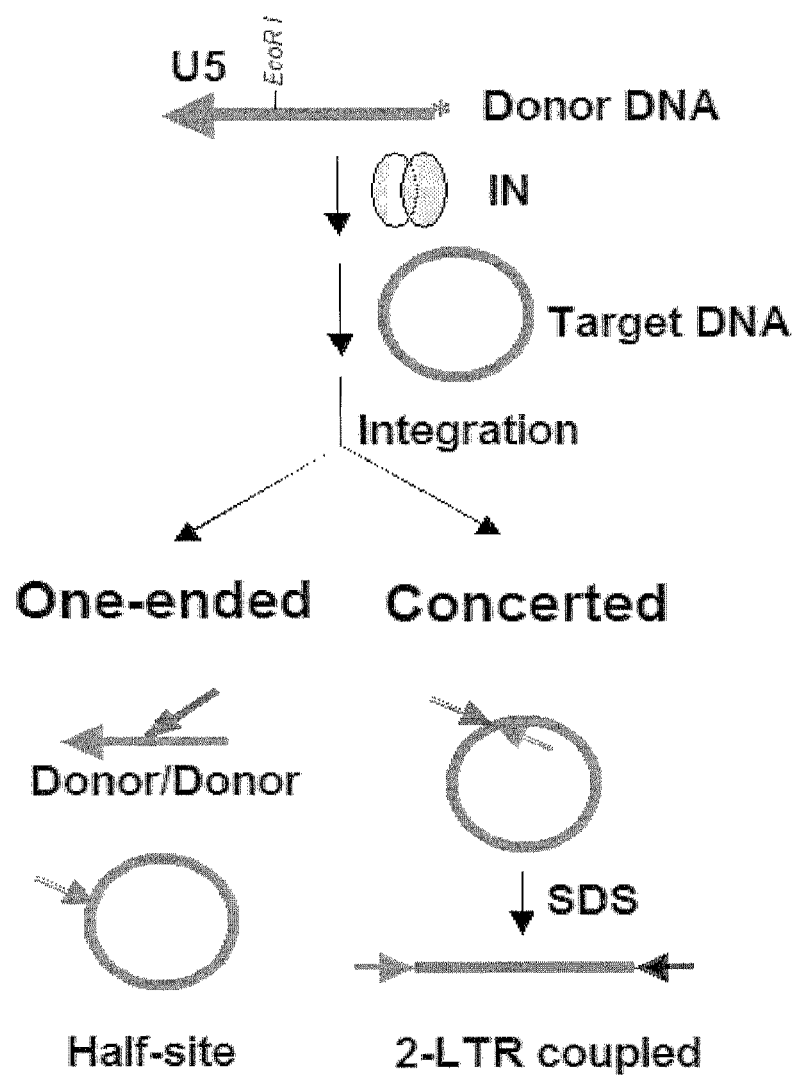
FIG. 2 shows a model for both half-site and concerted integration of a circular target DNA.

Generally, IN catalyzes a transesterification reaction; the 3' hydroxyl group of the viral DNA ends attack a pair of phosphodiester bonds in the target DNA. In a half-site integration reaction, viral integrase ligates one viral DNA end with one strand of the circular DNA target; in concerted integration two viral DNA ends are joined to a circular target resulting in linearization of the target DNA. FIG. 2 displays both the half-site and concerted integration of a circular target DNA. See Craigie, et al. *J. Biol. Chem.* (2005) 280(32):29334-9 and Craigie, et al. Retroviral DNA integration: reaction pathway and critical intermediates. *EMBO J.* (2006) 25(6):1295-304 and which are hereby incorporated by reference in their entirety for further details regarding this assay.

It was previously shown using this assay that processing by viral integrase directs the reaction pathway toward concerted integration and away from the half-site reaction pathway. It is thought that processing of the retroviral DNA by viral integrase facilitates the formation of a synaptic complex (i.e. viral integrase, retroviral DNA, genomic DNA, and various other endogenous proteins) that is competent for concerted integration.

Figure 3:
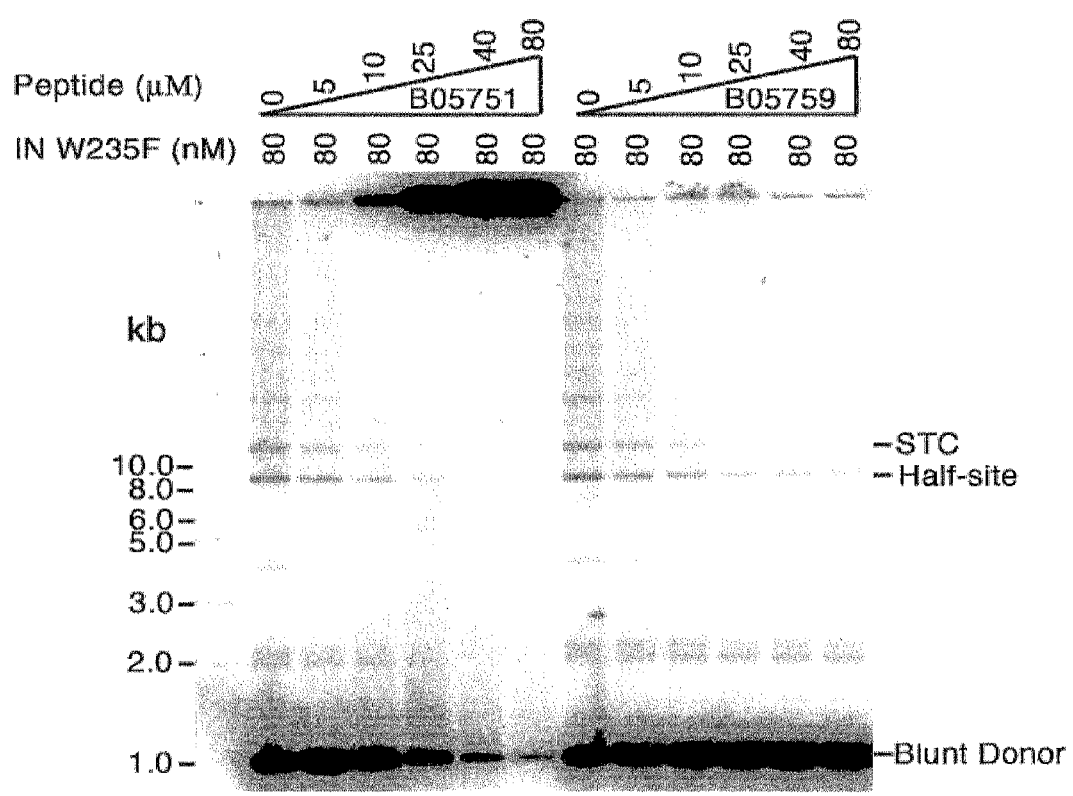
FIG. 3 shows an assay for concerted DNA integration without deproteinization.
Figure 4:
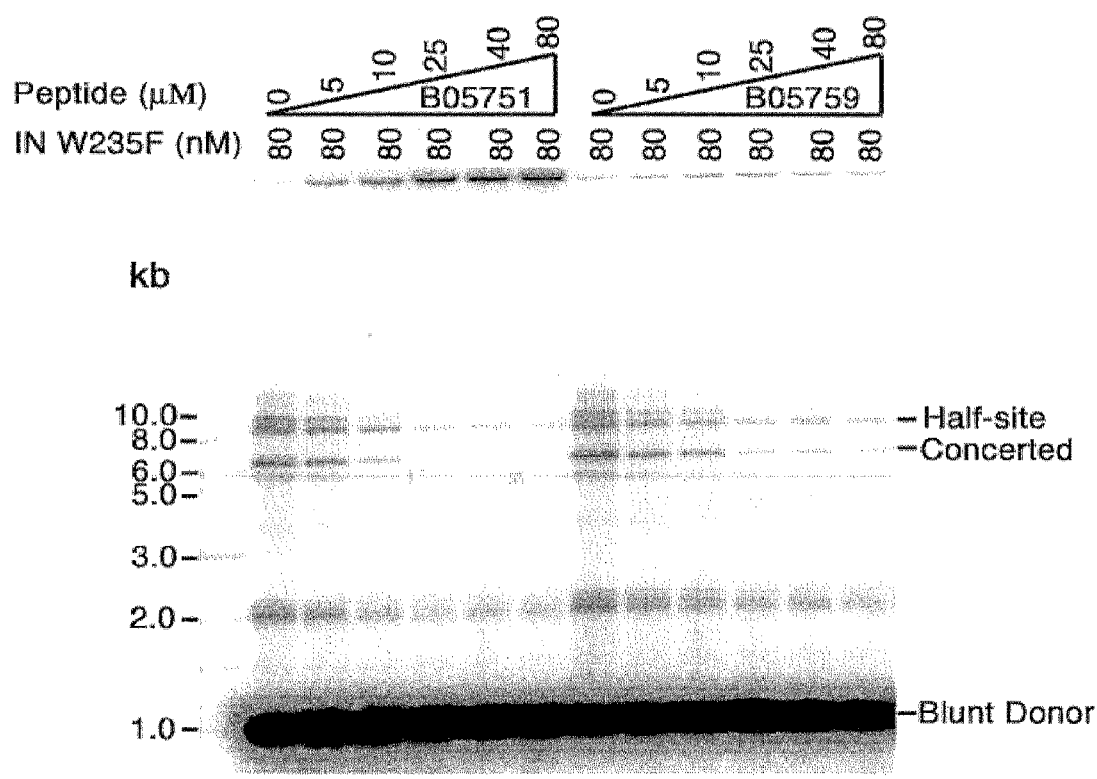
FIG. 4 shows an assay for concerted DNA integration with deproteinization.

In these experiments, either the peptide B05751 (SEQ ID NO:2) or the peptide B05759 (SEQ ID NO:3) was first mixed with HIV IN. B05751 (SEQ ID NO:2) has positively charged amino acids added to the end of the peptide to increase solubility, and B05759 (SEQ ID NO:3) has negatively charged amino acids added to the end of the peptide to increase solubility respectively. When either peptide was pre-incubated with IN, the peptide inhibited in-vitro concerted integration activity in the ~5 µM range. The peptide appeared to be blocking the assembly of a stable complex between viral integrase and the viral DNA ends. This was different from what is seen with strand transfer inhibitors such as MK0518 (with inhibitors such as MK0518 the strand transfer complex (STC) accumulates; however, this is not seen with the peptides described herein). FIG. 3 shows an assay for concerted DNA integration without deproteinization. In a concentration dependent manner, the STC was affected by both B05751 (SEQ ID NO:2) and B05759 (SEQ ID NO:3). FIG. 4 shows an assay for concerted DNA integration with deproteinization. In a concentration dependent manner, concerted viral DNA integration decreases as either B05751 (SEQ ID NO:2) and B05759 (SEQ ID NO:3) concentration increases. These results confirmed that SEQ ID NO:1, SEQ ID NO:2, and SEQ ID NO:3 inhibit the integration of viral DNA into the target DNA by interacting with HIV IN.

Figure 5:
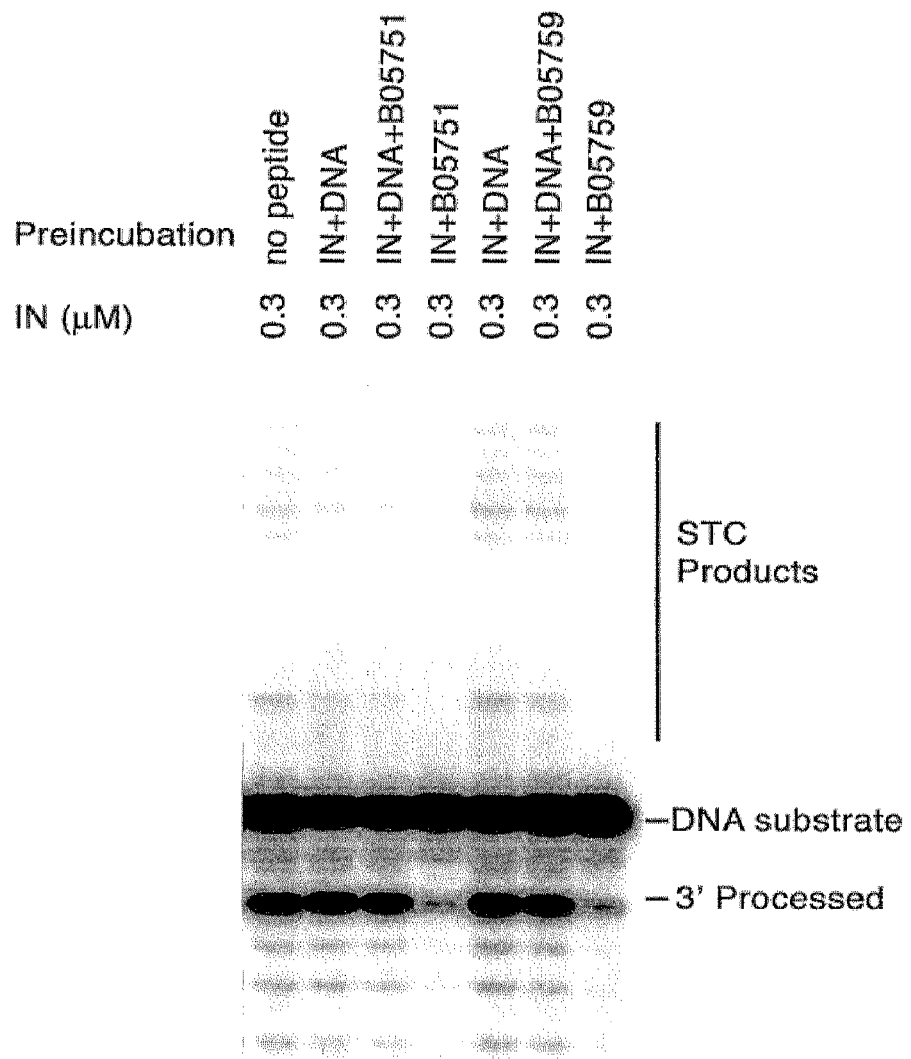
FIG. 5 shows that peptides described herein inhibit IN before the addition of DNA.

At this stage the mechanism of inhibition has not been fully elucidated. The peptide could stabilize the multimeric form of viral integrase or block dimer formation. In addition, the peptide inhibits when added to viral integrase before DNA, but not after adding DNA (FIG. 5). Since the peptide functions prior to the interaction of viral integrase with DNA, there may only be a short pharmaceutical window for which a theoretical synonymous drug may work.

Example 3

Screening for Chemical Inhibitors of IN

Using the yeast two hybrid system described above along with the peptide-IN interaction, chemical libraries can be screened under high throughput conditions for compounds that disrupt peptide-HIV IN interactions in yeast. Chemicals that interfere with the interaction between peptide and target will be identified by their ability to reduce reporter transcription. High-diversity chemical libraries are utilized that contain compounds from natural libraries (i.e. isolated compounds from marine organisms) and compounds of substantial purity with known drug-like properties. These will be screened either individually or in small pools (<10 compounds/pool) at concentrations of 10-100 µM. As a negative control for each compound or pool screened, these yeast cells will be screened against yeast cells that express an unrelated complex whose formation activates the reporter.

To select the best candidates for screening, selective hits, i.e. those compounds that reduce signal of the target-peptide strain but not the control strain, will be tested in a concerted integration assay for their ability to inhibit viral integrase activity.

Yeast LacZ assays will be performed as follows. Yeast strains will be grown to saturation by overnight incubation with shaking at 30° C. in 50 ml of selective media auxotrophic for tryptophan and leucine (supplemented with 2% dextrose). The yeast culture will then be diluted in selective media (supplemented with 2% dextrose) to a final OD600 absorbance value of 0.05. Sixty microliters of this cell suspension will be aliquoted into each well of a 384-well microplate (CliniPlate #11310-888, Thermolabsystems, Fi). 600 nl at 10 mM of chemicals (or neat DMSO in the case of the controls) will then be added onto the yeast in each well of the 384-well microplate. The 384-well microplates containing yeast plus chemicals will be grown in a Sterile Cult incubator for 18 hours. In addition to 320-wells containing target-peptide strain plus chemicals, each 384-well plate will contain 64 control wells as follows: 16 wells containing positive control strain plus 600 nl DMSO; negative control strain containing 600 nl DMSO; and 32 wells containing target-peptide yeast plus 600 nl DMSO. Following the incubation in the incubator, cells will be resuspend and the OD600 absorbance value of each well will be measured and recorded using a Saphire II microplate reader (Molecular Devices). Nine microliters of cells per-well will then be transferred into a black 384-well microplate (Matrical low volume MP101-1-PS, Spokane Wash.). Three microliters of YPER (Pierce Chemicals) will be added to each well (containing yeast). The plates will be incubated at room temperature for 30 minutes in order to allow for yeast lysis. To each well we will then add 22.5 µl of 1 mM CUG (β-galactosidase substrate, Molecular Probes) in Z-buffer (60 mM $Na_2HPO_4.7H_2O$, 40 mM $NaH_2PO_4.H_2O$, 10 mM KCl, 50 mM $MgSO_4.7H_2O$, 50 mM β-mercaptoethanol). The solution will be incubated for 30 minutes at room temperature following which 2.5 µl of 1M $Na_2CO_3$, added to stop the reaction. The fluorescence value of each well will then be measured and recorded using a Sapphire II reader (Tecan) with excitation at 390 nm and emission recorded at 460 nm with a 455 nm cutoff filter. Both the OD600 absorbance values and the fluorescence values will be subtracted for background and a normalized fluorescence value will be obtained by dividing the fluorescence value (for any given well) by the OD600 absorbance value (of the corresponding well). Other lacZ substrates may be used for detection of transcriptional activity from the reporter, for example, Beta-Glo (promega) which is a one step addition followed by a read 1 hr after addition to the cells.

A range of concentrations, initially focusing on the area between 10 and 100 µM will be tested. The final screening concentration will be selected such that true positives are recovered at a rate of ~1%, and the frequency of large negative effects on yeast growth may be low (<10%). Compounds will be diluted from master plates into working stocks at concentrations sufficient to yield a final assay concentration of 50 µM. Positives will be defined as signal (% RFU/OD 600) 40% lower than a DMSO control strain and growth 75% relative to control.

Positives will then be further screened by the concerted integration assay mentioned above. If these chemicals inhibit concerted viral DNA integration, these chemicals will be deemed viable inhibitors of HIV IN.

Example 4

Peptide Binds to Deletions of the N-Terminus and C-Terminus of HIV Integrase

To further gain an understanding of the mechanism of inhibition by the peptide, the location of the binding site(s) of the peptide was determined. Elucidation of the binding site(s) for the peptide could allow for use of fragments of integrase rather than the full length to be used in co-crystal studies with integrase, in-vivo displacement assays, and chemical screens in yeast. For example, if the peptide bound to two regions on integrase, it may be more difficult to isolate chemicals that block interaction of the peptide with integrase. To determine the region of interaction of the peptide of the present invention in HIV IN, six N-(pLBal3 (18-288), pBal4 (19-288), pBal8 (31-288), pBal5 (40-288), pLBal2 (43-288), pBal3 (48-288)) and four C-terminal deletion mutants (pCdelta1 (1-203), pBalC26 (1-210), pCdelta2 (1-220), pCdelta3 (1-215)) of IN were tested. The integrase fragments were fused to AC domains of GAL4 and tested for interaction in the two-hybrid system with the peptide fused to the GAL4 DNA binding domain. Construction of pLBal3, pBal4, pBal8, pBal5, pLBal2, pBal3, pBalC26 is described in Kalpana and Goff, Genetics 90:10593-10597 (1993) hereby incorporated by reference. Sequencing of C-terminal deletions show that a few additional non-IN amino-acids prior to the C-terminus of the protein, due to the position of the stop codon in the DNA plasmid.

Plasmids were transformed into base strain TSY 201 MATa ura3-52, his3-200, ade2-201, lys2-801, trp1-901, PDR5delta, SNQ2delta, leu2-3, 112, gal4-542, gal80-538 LYS2:: GAL2$_{UAS}$-GAL1$_{TATA}$-HIS3, URA3::GAL4$_{17mers(X3)}$-CyC1$_{TATA}$-lacZ. Interaction of the peptide with integrase would activate the expression of the lacZ reporter and result in accumulation of Beta-galactosidase in yeast; the interaction would also activation the HIS3 reporter allowing growth on synthetic plates lacking histidine. To determine the extent of the deletions of IN that retained the interaction with the peptide, strains harboring the plasmids were grown to mid-log in synthetic medium lacking leucine and tryptophan. Beta-Glo substrate from Promega, was added to measure the level of Beta-galactosidase activity in the yeast.

The Beta-Glo® Assay System consists of two components that are combined to form Beta-Glo® Reagent. This single reagent provides a coupled enzyme reaction system utilizing a luciferin-galactoside substrate (6-O-β-galactopyranosyl-luciferin). This substrate is cleaved by β-galactosidase to form luciferin and galactose. The luciferin is then utilized in a firefly luciferase reaction to generate light. Since a single reagent lyses cells and contains all of the components required to generate a luminescent signal that is proportional to the amount of β-galactosidase, many plates can be processed quickly and efficiently.

Figure 6:
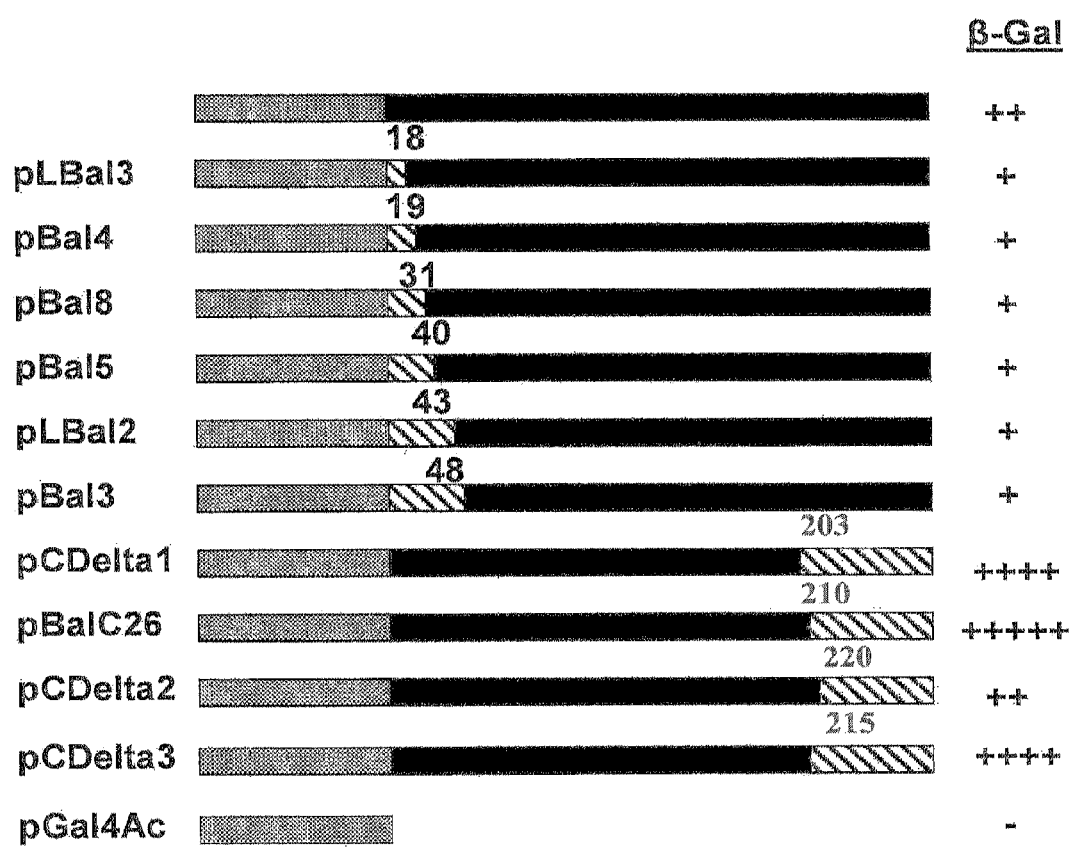
FIG. 6 shows that the peptide described herein can bind to IN lacking the N-terminus and can also bind to IN lacking the C-terminus.

The N-terminal deletions and wild-type showed measurable increase B-Gal activity suggesting IN bound to the peptide in the GAL4 system (FIG. 6). In addition, all of the C-terminal deletions interacted with the peptide in the DNA binding domain (FIG. 6). pCdelta1, pBalC26, pCdelta3 interacted even stronger to the peptide than full-length IN (FIG. 6). Geometrical constraints posed by the fusion protein may also contribute differences in activity due to the effect on either normal functioning of the GAL4 portion or the IN portion of the fusion protein.

It is to be understood that the above-described compositions and modes of application are only illustrative of preferred embodiments of the present invention. Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

F. Sequences

```
1.
                                                  SEQ ID NO: 1
LeuTyrGluThrIleLeuIleLeuLeuPheLeuAspValAspThrGly

2.
                                                  SEQ ID NO: 2
LeuTyrGluThrIleLeuIleLeuLeuPheLeuAspValAspThrGly

LysLysArg

3.
                                                  SEQ ID NO: 3
LeuTyrGluThrIleLeuIleLeuLeuPheLeuAspValAspThrGly

AspGluAsp

4.
                                                  SEQ ID NO: 4
LeuTyrGluThrIleLeuIleLeuLeuPheLeuAspValAspThrGly

XaaXaaXaa
```

What is claimed is:

1. A HIV integrase inhibiting peptide comprising an amino acid sequence having at least 90% sequence homology to SEQ ID NO: 1 or a variant thereof, wherein the variant consists of a deletion of the N-terminal residue or C-terminal residue.

2. The peptide of claim 1 having at least 90% amino acid sequence homology to SEQ ID NO: 1, SEQ ID NO: 2, SEQ ID NO: 3, or SEQ ID NO: 4.

3. The peptide of claim 2 comprising the amino acid sequence of SEQ ID NO: 1, SEQ ID NO: 2, SEQ ID NO: 3, or SEQ ID NO: 4.

4. The peptide of claim 1, wherein amino acids are independently selected from D-amino acids and L-amino acids.

5. The peptide of claim 1, wherein the amino terminus, the carboxyl terminus, or both the amino terminus and carboxyl terminus are modified.

6. The peptide of claim 5, wherein modification of the carboxyl terminus is acetylation or amidation, and wherein modification of the amino terminus is acetylation.

7. An isolated polynucleotide comprising a nucleotide sequence encoding an amino acid sequence having at least 90% sequence homology to SEQ ID NO: 1 or a variant thereof, wherein the variant consists of a deletion of the N-terminal residue or C-terminal residue.

8. The polynucleotide of claim 7, having at least 90% sequence homology to SEQ ID NO: 1, SEQ ID NO: 2, SEQ ID NO: 3, or SEQ ID NO: 4.

9. A method of inhibiting a HIV integrase activity, comprising contacting a HIV integrase with the peptide of claim 1.

10. A method of treating HIV in a subject, comprising administering to the subject the peptide of claim 1.

11. The method of claim 9, wherein the peptide comprises an internalization sequence.

12. A method of identifying a candidate agent that binds a HIV integrase comprising: (a) contacting at least one domain of a HIV integrase with the peptide of claim 1 under conditions that allow binding of the peptide to the integrase; (b) contacting the integrase with a candidate agent; and (c) determining whether the candidate agent displaced the peptide, wherein displacement of the peptide is an indication that the candidate agent binds to the integrase.

13. The method of claim 12, wherein the candidate agent is identified using a yeast two hybrid screening system, wherein transcriptional activation in a yeast is an indication that the peptide is binding the integrase.

14. The method of claim 12, wherein the candidate agent is identified using a yeast two hybrid screen, wherein a variation of expression of a reporter gene in a yeast is an indication that the candidate agent is disrupting the binding of the peptide to the integrase.

15. The method of claim 12, wherein the at least one domain of the integrase comprises a drug resistant mutation.

* * * * *

SEQUENCE LISTING

```
<160> NUMBER OF SEQ ID NOS: 4

<210> SEQ ID NO 1
<211> LENGTH: 16
<212> TYPE: PRT
<213> ORGANISM: Artificial Sequence
<220> FEATURE:
<223> OTHER INFORMATION: Synthetic Construct

<400> SEQUENCE: 1
```

```
Leu Tyr Glu Thr Ile Leu Ile Leu Leu Phe Leu Asp Val Asp Thr Gly
1               5                   10                  15

<210> SEQ ID NO 2
<211> LENGTH: 19
<212> TYPE: PRT
<213> ORGANISM: Artificial Sequence
<220> FEATURE:
<223> OTHER INFORMATION: Synthetic Construct

<400> SEQUENCE: 2

Leu Tyr Glu Thr Ile Leu Ile Leu Leu Phe Leu Asp Val Asp Thr Gly
1               5                   10                  15

Lys Lys Arg

<210> SEQ ID NO 3
<211> LENGTH: 19
<212> TYPE: PRT
<213> ORGANISM: Artificial Sequence
<220> FEATURE:
<223> OTHER INFORMATION: Synthetic Construct

<400> SEQUENCE: 3

Leu Tyr Glu Thr Ile Leu Ile Leu Leu Phe Leu Asp Val Asp Thr Gly
1               5                   10                  15

Asp Glu Asp

<210> SEQ ID NO 4
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (17)..(19)
<223> OTHER INFORMATION: Xaa can be any naturally occuring amino acid.

<400> SEQUENCE: 4

Leu Tyr Glu Thr Ile Leu Ile Leu Leu Phe Leu Asp Val Asp Thr Gly
1               5                   10                  15

Xaa Xaa Xaa
```